United States Patent [19]
Estell

[11] Patent Number: 5,244,791
[45] Date of Patent: Sep. 14, 1993

[54] METHODS OF ESTER HYDROLYSIS

[75] Inventor: David A. Estell, Mountain View, Calif.

[73] Assignee: Genecor International, Inc., South San Francisco, Calif.

[21] Appl. No.: 902,542

[22] Filed: Jun. 22, 1992

Related U.S. Application Data

[63] Continuation of Ser. No. 92,976, Sep. 3, 1987, abandoned, which is a continuation-in-part of Ser. No. 614,612, May 29, 1984, Pat. No. 4,760,025.

[51] Int. Cl.$^5$ .............................................. C12P 21/02
[52] U.S. Cl. .................................. 435/68.1; 435/219; 435/222; 435/220; 435/221; 930/240; 935/14
[58] Field of Search ................. 435/171, 68.1, 221, 435/222; 935/1, 10, 14, 29

[56] References Cited

U.S. PATENT DOCUMENTS

| | | | |
|---|---|---|---|
| 4,086,136 | 4/1928 | Isowa et al. | 435/68.1 |
| 4,760,025 | 7/1988 | Estell et al. | 435/222 |
| 4,800,162 | 1/1989 | Matoor | 435/280 |
| 5,002,871 | 7/1991 | Iacobucci | 435/68.1 |

OTHER PUBLICATIONS

Polgar et al. 1970. Adv. Enzymol. 33, 381–400.
Wells et al. 1983. Nuc. Acids. Res. 11, 7911-7923.
Wallace et al. 1981. Nuc. Acids. Res. 9, 3647-3656.
Rastetter, W. 1983. Trends Biotechnol. 1, 80–84.
Svendsen, I. 1976. Carlsberg. Res. Commun. 41, 237-291.
Robertus et al. 1972. Biochemistry. 11, 2439-2449.
Wells et al. 1986. Phil. Trans. R. Soc. Lond. 317, 415-423.
Breddam et al., 1980. Carlsberg Res. Commun. 45, 237-247.
Reich et al. (eds.) 1975. in: *Proteases and Biological Control.* Cold Spring Harbor Laboratory. Cold Spring Harbor; N.Y. pp. 1–11.
Phillip et al. 1983. Molec. Cell. Biochem. 51, 5-32.
Matthews et al. 1975. J. Biol. Chem. 250, 7120-7126.

*Primary Examiner*—Christopher S. F. Low
*Attorney, Agent, or Firm*—Margaret A. Horn

[57] ABSTRACT

A novel method for ester hydrolysis catalyzed by enzymes having an oxyanion hole wherein the amide hydrolysis reaction is minimized. Enzymes are selected or alternatively derived by replacement of amino acid residues, which have minimal hydrogen bonding at or within 15 angstroms of the oxyanion hole.

4 Claims, No Drawings

METHODS OF ESTER HYDROLYSIS

CROSS REFERENCE TO RELATED APPLICATIONS

This application is a continuation of U.S. patent application Ser. No. 092,976 filed Sep. 3, 1987 (abandoned), which is a continuation-in-part of U.S. patent application Ser. No. 614,612 filed May 29, 1984 (now issued as U.S. Pat. No. 4,760,025 which patent is incorporated herein by reference).

BACKGROUND OF THE INVENTION

1. Field of the Invention:

The present invention relates to a novel method for hydrolysis of esters and in particular to methods for making polypeptides via ester hydrolysis. The present invention uses novel enzymes to catalyze the ester hydrolysis which novel enzymes are selected and modified to have a amide hydrolysis rate which is significantly less than the ester hydrolysis rate. The invention further relates to enzymes and peptides made by the method of the invention.

2. Background Art

Many enzymes are known to catalyze ester hydrolysis. This type of hydrolysis reaction is useful, for example, in combining an ester of a given amino acid or peptide with another amino acid or peptide to form a polypeptide. It is hypothesized that a binding site in such enzymes exists which catalyzes this reaction. Likewise, these enzymes also catalyze amide hydrolysis, the reverse reaction, which acts as the yield limiting equilibrium reaction. Proteases, notably the serine proteases and thiol proteases are known to catalyze reactions which involve the catalytic triad of the enzyme. (Enzyme Structure and Mechanism, 2nd Edition, 1985, pp. 405-413). It is further understood that the intermediates in the reaction are probably stabilized by the "oxyanion hole" (Proteases and Biological Control, Reichet et al, 1975, pp. 5-27). The total mechanism of ester/amide hydrolysis is fairly well understood. It is known that interfering with this mechanism, for example by methylating a His 57 in the catalytic triad of chymotrypsin, that the reaction rates drop by a factor of 5,000-200,000. It has been assumed that this dropping activity is essentially equal for rates of hydrolysis for both amides and esters.

In Phil. Trans. R. Soc. Lond. A 317, 415-423 (1986), changes were also made for the first time in the amino acid residue comprising the oxyanion hole. In this instance, Ans-155 in subtilisin was modified to Thr, His, Gln and Asp by using a site specific mutagenisis of cloned subtilisin from B. Amyloliquefaciens. A large decrease in substrate turnover ($K_{cat}$) of 200-4,000 fold was observed for an amide substrate. However this was the only sustrate tested. Ester hydrolysis was not measured. Based on the mechanism and the prior art it would be logical to assume that the ester hydrolysis substrate turnover rate would also be reduced and the reduction would be proportional to the decrease amide hydrolysis. When selecting an enzyme for use in ester hydrolysis it would be useful to block or at least substantially reduce the equilibrium reaction toward amide hydrolysis. One way of accomplishing this is to have some method of removing the product before the amide hydrolysis can occur. Another theoretical way of accomplishing this would be to change the $K_{cat}/K_{cat}$ ratio for ester substrate verses amide substrate such that amide $K_{cat}$ is reduced to a greater extent than ester $K_{cat}$. Prior to applicant's invention the only possible way to alter one $K_{cat}$ more or less than the other $K_{cat}$ was to alter the reaction conditions i.e. pH. For example, in Carlsberg Res. Common Vol. 45, p. 237-247, 1980, Carboxypeptidase Y was used to catalyze peptide synthesis. The equilibrium of the competing reactions was changed by performing the reaction at high pH (i.e. >9). These conditions are obviously not advantageous for most enzymes which operate at lower pH, normally around neutral. It is interesting to note even further that the author notes that a single desired product is still not produced in high yield.

Accordingly, a method which uses an enzyme which is selective for ester hydrolysis over amide hydrolysis and operates at a variety of pH and other conditions would be useful.

SUMMARY OF THE INVENTION

It is an object of this invention to provide an enzymatic method of ester hydrolysis which minimizes amide hydrolysis without otherwise significantly altering the reaction conditions and consequently increases yields. It is further an object of the invention to provide a method of selecting enzymes which have high esterase activity and minimal amidase activity. It is also an object of the invention to provide a method of altering a protease so that substrate turnover ($K_{cat}$) for amidase activity is reduced such that $K_{cat}$ amidase/$K_{cat}$ esterase is lowered.

Accordingly, the invention provides a method of hydrolyzing an ester substrate comprising:

a) selecting an ester substrate;
b) selecting a protease having an oxyanion hole and capable of hydrolyzing the selected ester substrate wherein the amino acid sequence of said protease comprises a specific amino acid residue at or within 15 angstroms of the oxyanion hole having minimal hydrogen bonding characteristics with the proviso that the specific amino acid residue is not a member of a catalytic triad and with the proviso that the specific amino acid residue does not significantly structurally inhibit the binding characteristics of the protease to the ester substrate; and
c) reacting the selected protease with the selected ester substrate to hydrolyze said ester substrate.

The invention further provides a method for selecting a protease having high esterase activity relative to its amidase activity comprising:

a) selecting a protease having an oxyanion hole and comprising esterase and amidase activity;
b) screening the amino acid sequence at or within 15 angstroms of the oxyanion hole;
c) determining if the screened amino acid sequence has a specific amino acid residue therein with minimal hydrogen bonding characteristics with the proviso that the specific amino acid residue is not a member of a catalytic triad and with the proviso that the specific amino acid residue does not significantly structurally inhibit the binding characteristics of the protease to ester substrates; and
d) selecting the protease having high esterase activity relative to amidase activity when the results of the screening step c) are positive.

The invention also provides a method of increasing the esterase activity relative to the amidase activity of an enzyme comprising:

a) selecting a protease having an oxanion hole and having esterasae and amidase activity;
b) selecting an amino acid residue at or within 15 angstroms of the oxyanion hole with the proviso that the residue selected is not a member of a catalytic triad; and
c) replacing the selected amino acid residue with a different amino acid residue having less hydrogen bonding capabilities when compared with the selected amino acid residue with the proviso that the different amino acid residue does not significantly structurally inhibit the binding characteristics of the protease to ester substrates.

DETAILED DESCRIPTION OF THE INVENTION

As described above, enzymes have long been used to catalyze ester hydrolysis. It is also known that these enzymes also have amidase activity which is capable of hydrolysing amide portions of a molecule. When using an ester hydrolysis reaction to join amino acids in the making of polypeptides, the amidase acitivity often limits the yields achievable because of the enzyme attack on the amide portion or portions of the polypeptide. Applicant has suprisingly found that substrate turnover, $K_{cat}$ for ester substrates is reduced to a much lesser extent than is $K_{cat}$ for amide substrates when enzymes are selected or made with the characteristics as described herein. Thus relative enzyme turnover for this reaction and overall yield is much improved for ester hydrolysis over amide hydrolysis when compared with the results of previous or modified enzymes.

SELECTING ESTER SUBSTRATES

Esters, which are subject to attack by enzymes, are well documented in the literature. Almost any ester can be attacked and the ester portion hydrolyzed by an appropriate enzyme. Of particular importance are the amino acids, peptides and similar compounds which are useful in making polypeptides. Amino acids and peptides all have an amine group and a carboxyl group which can be alkylated to form an ester. Enzymes can be used to join esters of amino acids or peptides to other amino acids or peptides to form polypeptides. This is especially useful for making di- and tri-peptides such as the sweetener aspartame. Also this method would be useful for making peptide hormones. The invention of the application is especially valuable to increase the yield of such compounds because the enzyme used to make such peptides tends to degrade the amide portion or portions of the product. Decreasing the amidase activity by lowering the $K_{cat}$ of amidase activity relative to the $K_{cat}$ of esterase activity will increase yields. Accordingly, one could easily select a preferred ester substrate. Prefered ester substrates are those esters which either a) have an amide portion which is capable of being hydrolyzed, b) are used with another molecule having an amide portion capable of being hydrolyzed, or c) where the final product has an amide which is capable of being hydrolyzed.

SELECTING A PROTEASE

Enzymes of the invention are proteases having an oxyanion hole such as endoproteases most notably the serine and thiol hydrolases which catalyze reactions at selected sites in the presence of a neucleophile. These enzymes catalyze the hydrolysis of ester and amide bonds. The substrate (e.g. carboxylic acid ester) reacts with a catalytic amino acid of the catalytic triad of such serine or thiol hydrolases to give an intermediate in which the active site oxygen or thiol forms an ester linkage (acylenzyme) with the carbonyl group of the substrate. During hydrolysis, an amine portion acts as a nucleophile, and attacks the acyl enzyme to give free acid and enzyme. It has been discovered that the oxyanion hole plays a role in the stabilization of the reaction directly affecting substrate turnover, $K_{cat}$. While it was found in earlier works that changes in the area around the oxyanion hole would decrease the $K_{cat}$ in general, applicants have discovered that this decrease is not proportional and $K_{cat}$ for amide substrates is decreased to a much greater extent than for ester substrates. In subtilisin the catalytic triad is Asp 32, His-64, and Ser 221. The oxyanion hole is Asn-155 and Ser 221. Changes in the amino acid residue at Asn 155 to Thr, His, Asp, Gly or Ala decrease $K_{cat}$ for ester substrates by a factor of 2 and for amides by a factor of 200. Thus ester hydrolysis is much more favored than amide hydrolysis. In chymotrypsin the catalytic triad is Asp-102, His 57 and Ser 195 and the oxyanion hole is Gly 193 and Ser 195. Other protease might include trysin, V8-protease, papain, caltepsin, bromelain, or carboxypeptidase Y. Generally though the catalytic triad oxyanion hole can be identified from the crystal structure or from chemical methods (see Means, G. and Feeny, R., Chemical Modification Proteins, Holder-Day, Inc.). Preferred proteases are the serine and thiol proteases, notably subtilisins. Other proteases with oxyanion holes and which catalyze esterase and amide reactions can therefore be readily identified by one skilled in the art. Applicants have discovered a unique mechanism that depends on the general function (i.e. oxyanion hole) and not the specific nature of the enzyme.

SELECTION OF A SPECIFIC AMINO ACID RESIDUE

Once the protease is chosen, it must be decided or in most cases modified to have the proper characteristics. The amino acid residues within about 15 angstroms of the oxyanion hole are identified. Enzymes have numerous folds and bends in the structure and one would in general use the crystal structure of the enzyme to determine which amino acids are within the 15 angstrom limit, regardless of the primary structure of the enzyme. Where no crystal structure is available, residues in the primary sequence about 6 amino acids on either side of one of the amino acid residue that comprise the oxyanion hole or the oxyanion hole amino acid residues themselves would be within the 15 angstrom requirement. Only where such residue is a member of the catalytic triad is the residue not considered. Changes to the catalytic triad would inactivate the enzyme.

Once the sites are identified within the considerations of the invention each of the sites is reviewed for, or one of the sites is selectively replaced with an amino acid residue with low hydrogen bonding characteristics and where a replacement residue is made lower bonding characteristics then the original residue. In addition, the replacement residue must not sterically interfere with the enzymes ability to hydrolyze esters by blocking the oxyanion hole site or nearby sites. This generally means no large groups such as phenyls or the like which may block the binding site or alter the shape of the site can be chosen. Preferably the amino acid residues selected to replace residues are Thr, His, Asp, Gly and Ala. Most preferred is Gly. In a prefered embodiment the oxyanion hole residue which is not also a catalytic triad member is modified or selected with one of the above amino acids. One skilled in the art would easily be capable of selecting or replacing such residue. Specifically prefered is selecting subtilisin enzyme modified or selected at Asn 155 with Thr, His, Asp, Ala or especially Gly.

REACTION OF THE ENZYME WITH AN ESTER

Once the enzyme is selected or modified according to the invention it is a simple matter to use it as a catalyst in an ester hydrolysis reaction. One skilled in the art would be able to make di and tripeptides, peptide hormones and the like. The following examples are representative of the invention and not intended to be limiting. One skilled in the art would be able to make changes in the methods, procedures, enzymes selected, etc. based on the disclosure herein.

DESCRIPTION OF THE PREFERRED EMBODIMENTS

The kinetic constants $K_{cat}$ and $K_m$ were determined for enzymatic hydrolysis of peptide and ester substrates by the bacterial serine protease subtilisin BPN' and its variant enzyme, N155G. Measurements were performed at 25° C. using a Hewlett-Packard 8451A diode array spectrophotometer equipped with a jacketed cuvette holder. Enzyme concentrations were determined spectrophotometrically. The substrate used for measuring enzyme catalyzed peptide bond hydrolysis was succinyl-L-Ala-L-Ala-L-Pro-L-Phe-p-nitroanilide (sAAPFpna) obtained from Sigma. Stock solutions of the substrate sAAPFpna were prepared in dimethyl sulfoxide at concentrations of 10 and 100 mg/ml. Reactions are initiated by adding 10 µl concentrated pure enzyme to a 1 cm cuvette containing substrate (10 µl of stock solution) in 0.98 ml of 0.1M Tris buffer, pH 8.6, with 0.005% Tween 80. Separate reaction time course data were obtained for the 10 and 100 mg/ml substrate stock solutions using the same level of enzyme in each experiment. The appearance of p-nitroaniline was detected at 430 nm (ext. coeff.=3723) for the low substrate concentration progress curve and at 460 nm (ext. coeff.=375) for the high substrate curve. At pH 8.6, non-enzymatic base hydrolysis of the substrate was negligible for the duration of the analysis. Data for reaction progress curves was measured at regular intervals and pairs of absorbance-time values stored in memory. Upon completion of the reaction, data from each time course measurement was derivatized and a plot of reaction velocity versus product concentration is fit to the differential form of the rate equation using a non-linear least squares fitting routine.

Performing two progess curve measurements at different initial substrate levels allows for the estimation of $K_m$ to be corrected for the influence of peptide product inhibition. The substrate used for analyzing enzyme catalyzed ester bond hydrolysis is succinyl-L-Ala-L-Ala-L-Pro-L-Phe-thiobenzyl ester (sAAPFsbz) obtained from Bachem. Stock solutions of the substrate sAAPFsbz were prepared in dimethyl sulfoxide at concentrations of 20 and 200 mg/ml. In addition, a stock solution of 0.075M Ellman's reagent (5,5'-dithiobis-(2-nitrobenzoic acid)) in dimethyl sulfoxide was prepared. Initial reaction rates were measured for a fifteen second time period at 410 nm. Reactions were initiated by adding 10 µl of pure enzyme to a 1 cm cuvette containing 5 µl Ellman's reagent, 5 µl of substrate stock solution and 0.98 ml of 0.1M Tris buffer, pH 8.6, with 0.005% Tween 80. Final enzyme concentration in the reaction mixture was adjusted such that substrate depletion for the duration of the ratemeasurement was kept below 5% of the initial substrate concentration. Kinetic parameters were calculated from the average initial reaction velocities obtained for the two different substrate levels.

| Comparison of kinetic parameters for ester and peptide substrates: | | | | |
|---|---|---|---|---|
| Enzyme/$K_m$ | Substrate | $K_{cat}$ ($s^{-1}$) | $K_m$ (M) | $K_{cat}$ ($s^{-1}M^{-1}$) |
| Asn155 (WT) | sAAPFsbz | 2800 | $6.8 \times 10^{-5}$ | $4.2 \times 10^7$ |
| | sAAPFpna | 50 | $1.4 \times 10^{-4}$ | $3.6 \times 10^5$ |
| Gly155 | sAAPFsbz | 1300 | $6.7 \times 10^{-5}$ | $1.9 \times 10^7$ |
| | sAAPFpna | 0.25 | $1 \times 10^{-4}$ | $2.6 \times 10^3$ |

ENZYMATIC PEPTIDE SYNTHESIS

Materials

L-tryptophan methyl ester (W-OMe), L-leucinamide (L-NH$_2$), L-alaninamide (A-NH$_2$), glycinamide (G-NH$_2$), L-trytophyl-L-trytophan (W-W), L-tryptophyl-L-leucine (W-L), L-tryptophyl-L-alanine (W-A), and L-tryptophylglycine (W-G) are all obtained from Sigma Chemical Company. The wild type and mutant enzyme Asn→Gly 155 (Gly155) are prepared as described in U.S. Pat. No. 4,760,025 issued Jul. 26, 1988.

A 1M stock solution of W-OMe is prepared in milli-Q water and the pH adjusted to 7.0. 1M stock solutions of the amino acid amides L-NH$_2$, A-NH$_2$, and G-NH$_2$ are also prepared in milli-Q water with the pH adjusted to pH 8.0. Stock solutions of the peptide standards W-W, W-L, W-A, and W-G are prepared at 10 mg/ml in milli-Q water. All stock solutions are stored at −20° C.

Method

Substrate mixes for peptide synthesis contain 0.25 ml of W-OMe 1M stock solution, and 0.05 ml of one of the 1M amino acid amide stock solutions. Enzyme is added to this solution at a final concentration of 0.2 mg/ml. Reactions are carried out at room temperature and 0.05 ml aliquots are removed at regular time intervals and diluted with 0.45 ml of 0.1M sodium phosphate, pH 2.0. A control sample consists of the reaction mixture without enzyme. Analysis of the quenched samples is by HPLC separation of the reaction components. From the diluted samples 0.05 ml is injected onto the column and a flow rate of 1 ml/min is maintained for a total run time of 25 minutes. Absorbance of the eluent is monitored at 254 nm. Peptide products are identified by comparing the retention times of the standards W-W, W-L, W-A, and W-G. The HPLC system used consists of an IBM model 9560 liquid chromatograph system, a Waters model 481 detector, a Waters Wisp 710B sample autoinjector, and an Altex C-8 reverse phase column (4.6 mm×25 cm). The solvent system consists of an isocratic delivery of 68% 0.1M sodium phosphate +0.01M pentane sulfonic acid, pH 2.0; 16% acetonitrile; and 16% methanol.

What is claimed is:

1. An improved method for making a peptide by enzyme hydrolysis, the improvement comprising:
    a) identifying a modified subtilisin having high esterase activity relative to amidase activity, wherein the modified subtilisin is substituted at the residue position equivalent to Asn+155 of *Bacillus amyloliquefaciens* subtilisin with an amino acid having low hydrogen bonding characteristics, said substitution resulting in an alteration of $K_{cat}$ for esters by a factor of at least about 2 and an alteration of $K_{cat}$ for amides by a factor of at least about 200 as measured using the synthetic peptide substrates, of succinyl-L-Ala-L-Ala-L-Pro-L-Phe-p-nitroanilide and succinyl-L-Ala-L-Ala-L-Pro-L-Phe-p-thiobenzyl ester and b) reacting an appropriate amount of the modified subtilisin of step a) with an amino acid ester substrate under conditions suitable for enzymatic hydrolysis.

2. A method of claim 1 wherein the substituted amino acid is selected from the group consisting of: Thr, His, Asp, Gly, or Ala.

3. The method of claim 2 wherein the modified subtilisin contains a Gly in place of the Asn at position 155.

4. A method of claim 1 wherein the peptide prepared by such process is a polypeptide.

* * * * *

UNITED STATES PATENT AND TRADEMARK OFFICE
CERTIFICATE OF CORRECTION

PATENT NO. : 5,244,791
DATED : September 14, 1993
INVENTOR(S) : David A. Estell

It is certified that error appears in the above-indentified patent and that said Letters Patent is hereby corrected as shown below:

On the title page, item [75]:
Inventor: after "David A. Estell, Mountain View, Calif."
add --Thomas P. Graycar, Pacifica, Calif.--

Signed and Sealed this

Nineteenth Day of July, 1994

Attest:

BRUCE LEHMAN

*Attesting Officer*    *Commissioner of Patents and Trademarks*